United States Patent [19]

Kliegman et al.

[11] 4,328,026

[45] May 4, 1982

[54] PHOSPHORANYL DERIVATIVES CONTAINING NITROGEN

[75] Inventors: Jonathan M. Kliegman, Wayne; Robert F. McCarthy, Red Bank, both of N.J.

[73] Assignee: GAF Corporation, New York, N.Y.

[21] Appl. No.: 7,769

[22] Filed: Jan. 30, 1979

Related U.S. Application Data

[63] Continuation-in-part of Ser. No. 935,945, Aug. 23, 1978, abandoned, and Ser. No. 940,211, Sep. 7, 1978, abandoned.

[51] Int. Cl.$^3$ .................... A01N 57/16; C07F 9/65
[52] U.S. Cl. ............... 71/86; 260/239 EP; 260/936; 546/25; 525/336; 525/340; 260/239.3 R; 260/239.3 A; 548/413
[58] Field of Search ........... 260/326.5 A, 239 EP, 260/239 AR, 936; 525/336, 340; 71/86; 546/25

[56] References Cited

FOREIGN PATENT DOCUMENTS 2840063 3/1979 Fed. Rep. of Germany .

Primary Examiner—Anton H. Sutto
Attorney, Agent, or Firm—James Magee, Jr.; Marilyn J. Maue

[57] ABSTRACT

In one aspect the invention relates to the complexed product of the reaction between a haloalkylphosphonic acid and an amide of the structure $R^3$—CO—N($R^1$)($R^2$) where $R^1$, $R^2$ and $R^3$ are as defined below. In another aspect the invention relates to the phosphoranyl derivatives indicated to have the structure:

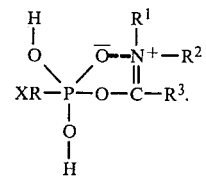

wherein R is lower alkyl; X is a halogen atom such as fluorine, chlorine, bromine, or iodine; $R^1$, $R^2$ and $R^3$ are each independently hydrogen, phenyl, naphthyl, methyl or ethyl substituted phenyl, alkyl or 1 to 24 carbon atoms optionally substituted with hydroxy or halogen and $R^1$ can additionally be alkylene of 2 to 4 carbon atoms; or $R^2$ and $R^3$, together with nitrogen, can form a N-heterocyclic ring having from 3 to 5 carbon atoms, which ring may be saturated or unsaturated; and the polymer of the above compound when $R^1$ is vinyl and $R^2$ and $R^3$ form said N-heterocyclic ring; or a mixture containing said phosphoranyl derivative. In another aspect the invention relates to a polymeric compound indicated as containing the unit:

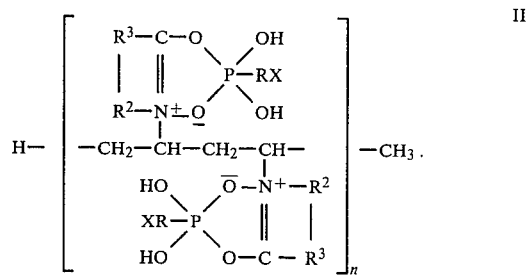

wherein n is 1 to 5000; or a mixture containing said polymeric complex. The invention also pertains to the process of applying a growth regulating amount of at least one said complexed compounds to a plant or plant situs.

38 Claims, No Drawings

PHOSPHORANYL DERIVATIVES CONTAINING NITROGEN

This application is a continuation-in-part of, copending application, Serial No. 935,945 filed Aug. 23, 1978, and copending application Serial No. 940,211 filed Sept. 7, 1978, both now abandoned.

The present invention relates to and has for its objects the production of phosphoranyl derivatives containing a nitrogen atom as novel compounds which are useful as agricultural products for plant growth regulation effecting growth promotion, growth inhibition, and maturation dependent upon the concentration of the present compound with respect to the plant. The compounds of the present invention are ethylene-releasing and/or ethylene stimulating agents, generally inducing the hormonal effects known for ethylene as described in many texts which are incorporated herein by reference, for example, ETHYLENE IN PLANT BIOLOGY, by F. B. Abeles, Academic Press, Inc., 1973, particularly Pages 103 through 215. Specific promotional effects include earlier bud break, synchronization of fruit ripening and leaf drop, temporary increase in tree sap or latex flow, breaking of dormancy in treated seeds, bulbs, tubers and corns. Inhibitory effects include defoliation, stunting and control of apical dominance. The compounds of the present invention are particularly effective in the treatment of tobacco, cotton, wheat, vegetables, fruit and rubber trees. The treatment of cotton, for example, is set forth in applicant's copending parent application, Ser. No. 833,757 filed Sept. 17, 1977 on the treatment of Gossypium, particularly the disclosure on pages 6 through 37 inclusive, which is incorporated herein by reference.

According to the present invention, there is provided compounds indicated by analysis to possess the formula:

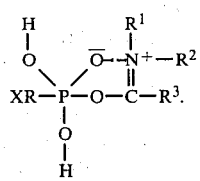

wherein R is lower alkyl; X is a halogen atom such as fluorine, chlorine, bromine, or iodine; $R^1$, $R^2$ and $R^3$ are each independently hydrogen, phenyl, naphthyl, lower alkyl substituted phenyl, alkyl or 1 to 24 carbon atoms optionally substituted with hydroxy or halogen and $R^1$ can additionally be alkylene of 2 to 4 carbon atoms; or $R^2$ and $R^3$, together with nitrogen, can form a N-heterocyclic ring having from 3 to 5 carbon atoms, which ring may be saturated or unsaturated; and the polymer of the above compound when $R^1$ is vinyl and $R^2$ and $R^3$ form said N-heterocyclic ring, preferably a pyrrolidone ring. This polymeric compound of the present invention is believed to contain the unit:

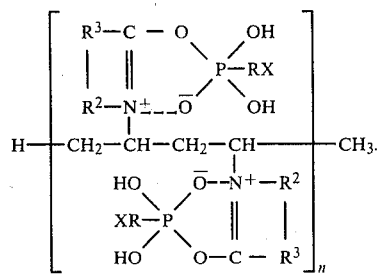

where n is 1 to 5000 and additionally may contain units of the unsubstituted N-vinyl heterocyclic ring and/or units of a derivative of the above dimer which is monosubstituted with the haloalkyl-dihydroxy phosphoryl group.

Of the complex compounds of this invention, those formed from a 2-haloethyl phosphonic and a cyclic amide are preferred. Most preferred are the complexes of 2-haloethyl phosphonic acid and N-methyl-2-pyrrolidone.

In the above formulae, it is to be understood that ionic charges can be neutralized to extinction and that such neutralized compounds are also within the scope of this invention.

The compounds of the present invention are prepared by reacting a haloalkyl phosphonic acid, i.e. corresponding to that moiety in the product desired, and an amide, e.g. polyvinyl pyrrolidone or the amide corresponding to the amide moiety of the product desired, at a temperature from about the freezing temperature of the reaction mixture to about 225° C., preferably from about 0° C. and about 200° C. under between about 10 psig and about 150 psig. In general the reaction involving the above-described reactants is postulated as follows:

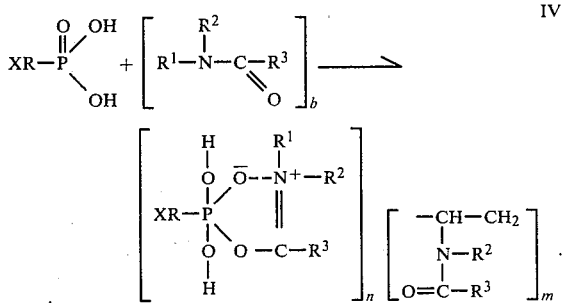

wherein X, R, $R^1$, $R^2$ and $R^3$ are as described in Formula I; b has a value of between 2 and about 5500 when $R^1$ is vinyl and $R^2$ and $R^3$, with N, form a heterocyclic ring and otherwise b is 1; n is 1 and m is zero, except when a heterocyclic polymeric reactant is employed. In the later case, n has a value of 2–5000 and m is 1–5000 and the n and m recurring units may be distributed in random or block configuration in the polymeric product.

While the structures presented above have been indicated by various analytical procedures, including infrared anaylsis, elemental analysis, H1, C13 and P31 nuclear magnetic resonance spectroscopy, titration analysis and dissociation analysis, applicants do not wish to be bound to any particular structure and considers their invention to reside in any compound formed from the reaction between a haloethylphosphonic acid and the amides defined herein. It is further postulated that the above described compound may be in equilibrium or admixture with other complex or polymeric forms.

The phosphonic acid and amide reactants are introduced into the reactor in a mole ratio of between about 0.2:1 and about 4:1, preferably a mole ratio of between about 1:1 and about 3:1, based on phospho:amido moieties. The reaction may be extremely rapid in the absence of a diluent. However, the rate of reaction can be reduced by employing a solvent for the reaction such as an ether, ketone, chlorinated or nonchlorinated liquid hydrocarbon, O-heterocyclic compound, water or any inert liquid solvent or dispersant. Suitable solvents include methyl ethyl ether, diethyl ether, methyl ethyl ketone, diethyl ketone, chloroform, carbon tetrachloride, benzene, toluene, xylene, tetrahydrofuran, furfuryl, cyclohexane, hexane, heptane, octane, etc. Most desirably, the reaction is effected in the presence of a solvent in which the product is insoluble. While the complex of the present invention may partially dissociate in water when in very dilute solutions of less than 2 moles of complex to 3 moles of water, the complex is reformed upon evaporation of water.

The reaction is carried out under anhydrous or nonanhydrous conditions, preferably with agitation and is completed within a period of not more than two hours to provide from about 90% to about 100% conversion to product. It is most preferred to dissolve each of the reactants in the chosen solvent to provide a solution of the reactant having between about 20 and about 60 weight percent concentration therein. The respective reactant solutions are then mixed in the reactor, desirably at ambient temperature under atmospheric pressure. Formation of the product may be indicated by the separation of an oil phase which settles to the bottom of the reactor when a solvent is selected in which the product is insoluble. After reaction is complete, the upper solvent layer is withdrawn and the oil recovered as a product of the process. When the solvent is one in which the product is soluble, it can be removed from the product by evaporation, stripping, extraction or by any other convenient or conventional method. However, it is to be understood that it may be desirable to leave the product in solution to be used directly as a plant growth regulating composition. In general, the reaction is completed within a period of not more than 2 hours, and more often within about 40 minutes.

When employed as agricultural aids, the products of the present process, for economic considerations, are usually combined with various inert carriers and extenders, for example, they may be mixed with talc, clays and various other conventional dry particulate solids to form pastes, dusts, or heavy oily substances which may beneficially adhere to the plant in climates of high rainfall. Alternatively, the compounds of the present invention may be extended with inert liquid carriers which include emulsions or solutions of any of the foregoing reaction solvents and solutions with mineral or vegetable oils or they may be extended with water or aqueous solutions of organic solvents. The concentrations of the present compound in the carrier can vary between about 15 ppm and about 150,000 ppm, preferably between about 25 ppm and about 100,000 ppm depending upon the effect desired. The resulting composition of active agent and carrier may be applied to the plant at a rate of between about 0.1 and about 100 Kg/hectare, preferably between about 0.5 and about 50 Kg/hectare of soil area for promotional effects and higher amounts for inhibiting effects.

The complex compounds of the present invention can be applied to plants as a particulate solid or as a liquid. When liquid application is desired, the present compound may be used as a preformed solution or the complex may be formed on a plant part or plant situs subjected to treatment, e.g. as when a solution of the haloethylphosphonic acid and a solution of the amide are applied as separate sprays so that the complex is formed on the plant or plant situs when the respective solutions contact each other. It is also to be understood that various methods of application can be employed, such as e.g. spraying, dipping, etc. as well as dry applications which may entail dusting, broadcasting, or any other convenient method of application.

It is also to be understood that the composition containing the present compound or one of the treating solutions may optionally contain other additives such as a surface active agent, a thickener, and/or other agricultural chemicals such as, for example, an algicide, a fungicide, an herbicide, an insecticide, a nematocide, a disinfectant, or a plant growth regulant; or any mixture of these. Preferably, when such mixtures are used, the added agricultural agents are those which do not materially lower the activity of the present complex. Exemplary of other agricultrual agents which may be employed with the compounds of the present invention include tributylphosphortrithio -ate or -ite (DEF or FOLEX); 1,1-dimethyl-4,4'-bipyridinium salts, e.g. the methyl sulfate salt or halide salt (Paraquat); sodium chlorate; an alkali metal salt of cacodylic acid, e.g. the sodium salt BOLL's-EYE; chlorinated isophthalonitriles, e.g. the tetrachlorinated derivative, Daconil; alkyl-1-(butylcarbamoyl)-2-benzimidazole carbamate, e.g. the methyl derivative, Benomyl; dialkylaminobenzenediazo alkali metal sulfates, e.g. the dimethyl derivative, Dexon; 2,4-dinitro-6-alkylphenyl-crotonate, e.g. the octyl derivative Karathane; manganese ethyl bis(dithiocarbamate), e.g. Maneb or Manzate; 2,3-dihydro-5-carboanilido-6-methyl-1,4-oxathiin-4,4-dioxide, (Plantvax); polychloronitrobenzenes, e.g. the pentachloroderivative Terraclor; 5-ethoxy-3-trichloromethyl-1,2,4-thiadiazole, Terrazole; 5,6-dihydro-2-methyl-1,4-oxathiin-3-carboxanilide, Vitavax; tetramethylthiuram disulfide, Arasan; N-(acyl-tert.-amidoalkyl) anilides, such as Lasso; esters of cyclopropane substituted carboxylic acids; alkylsulfinyl substituted diphenylethers; alkyl-1,2-dimethyl-3,5-diphenyl pyrazolium salts and derivatives thereof; diethyl amino-2,6-dinitro-4-trifluoromethylbenzene, and derivatives such as the amino substituted derivative Cobex; dinitroanilines; trifluoromethyl-nitro-diphenyl ethers; halo-N-cyclicimidoalkylene-substituted acetanilides; dichloronitrobenzoic acid and derivatives thereof, e.g. Dinoben; phosphonium salts, such as Phosphon; halogenated benzoic acids, such as 2,3,6-TBA or Benzac, 2,4-D and 2,4,5-T; aminodihalobenzoic acids, such as Amiben; polychlorophenyl-nitro-phenylate ethers, such as Modown; 6-benzyl-aminopurine (Benzyladenine); arylazomalononitriles; dimethylformamide; methyl acetamide; dimethylacetamide; 2-propyl-2-chloroethyltrifluorodinitropropyl toluidine (Basalin); N,N-bis (phosphonomethyl) glycine (Glyphosine); 5-chloro-3-methyl-4-nitro-1H-pyrazole; 2-chloroethyltrimethyl ammonium chloride (Cycocel or CCC); 2-(3-chlorophenoxy) propionic acid (3-CPA); 4-chlorophenoxyacetic acid (4-CPA); 3-(chlorophenyl)-1,1-dimethylurea (Monuron); N-dodecyl guanidine acetate, (Dodine); urea; 2-haloethylphosphonic acid, e.g. ethephon; 3-amino-1,2,4-triazole; cycloheximide; 2-(3-chlorophenoxy) propionamide; maleic hydrazide (1,2-dihydropyridazine-3,6-dione); ammonium thiocyanate; the alkali metal salt of 2,3-dichloro-2-methyl propionic acid, (e.g. the sodium salt Mendok); 3-(3,4-dichlorophenyl)-1,1-dimethylurea (Diuron); 6,7-dihydrodipyrido pyrazidinium dibromide (Diquat); maleic hydrazide; 2,4-dinitro-6-sec-butyl-phenol (Dinoseb); cycloheximide; N-2,4-dimethyl-5-(trifluoromethyl)-sulfonylamino phenyl acetamide (Mefluidide); haloalkyl silanes; 6-furfurylaminopurine (Kinetin); 4-hydroxyethyl-hydrazine (BOH); 1-hydroxytriacontane; 3-indoleacetic acid (IAA); 3-indolebutyric acid (IBA); abscisic acid (ABA); 1-naphthaleneacetic acid (NAA); dieldrin-hexachloro-epoxy-octahydro-endodimethannaphthalene (Endrin); the 2,4-dichlorophenyl ester of benzene (Genite); N-[(tetrachloroethyl) thio]4-cyclohexene-1,2-dicarboximide, (Difolatan 4F); monosodium acid-methane arsonate (MSMA); trichlorophenyl-acetic acid alkali metal salt (Fenac); 2-naphtoxyacetic acid (BNOA); the alkyl amine salt of succinic acid or of 7-oxabicycloheptane-2,3-dicarboxylic acid (Endothall); succinic acid-2,2-dimethyl hydrazine (SADH or Alar); gibberellic acid (Activol or Gibrel); 2,3,5-triiodobenzoic acid (TIBA); iron chelate; sulfur; nicotine sulphate; lead arsinate; self-emulsifying petroleum oil; sodium selenate; zinc ethylene bisdithio-carbamate (Zineb); tetramethyl thiuramdisulfide (THIRAM); N-trichloromethylthiotetrahydro-phthalimide (Captan); mercaptobenzolthiozole (Rotax); 1,1,1-trichloro-2,2-bis(chlorophenyl) ethane (DDT); 2-(2,4,5-trichlorophenoxy) propionic acid (Silvex); 3,6-dichloro-o-anisic acid (Dicamba); 2,2-dichloropropionic acid (Dalapon); 2-chloro-4,6-bis(ethylamino) S-triazine (Simazine); N,N-diallyl-2-chloroacetamide (CDAA); 2-chloroalkyldiethyl-dithio carbamate (CDEC); dimethyltetrachloro teraphthalate (DCPA or Dacthal); N,N-dimethyl-2,2-diphenyl acetamide (Diphenamide); dimethyldithiocarbamate (Ferbam or Ziram); malathion; actidione, zinc dimethyldithiocarbamate (Ziram); hexahydromethanoindene (Chlorodane); chlorinated dimethanonaphthalene)(Dieldrin or Aldrin); sodium N-methyldithiocarbamate dihydrate (Vapam); 2,2-dichlorovinyl dimethyl phosphate (Vapona or DDVP); O-(2,4-dichlorophenyl)-O-methyl isopropyl phosphoramidothiate (Zytron); arsenic trioxide mixtures (Sodite); posphomolybdic acid (PMA); O,O-diethyl-O(2-isopropyl-6-methyl-4-pyrimidinyl) phosphorothioate (Diazinon); 1,1-bis(chlorophenyl)-2,2,2-trichloroethanol (Kelthane); 2,2-bis(p-methoxyphenyl)-1,1,1-trichloroethane (Methoxychlor or DMDT); 2,4,4',5-tetrachlorodiphenylsulfone (Tedion); O,O-diethyl-O- (and S-)-2-(ethylthio) ethyl phosphorothioates (Systox); isopropyl-N-(3-chlorophenyl) carbamate (chloro-IPC or CIPC); sodium 2,4-dichloro-phenoxyethylsulfate (SES or Sesone); Bordeaux mixture; preparations containing streptomycin (Agrimycin); N-trichloromethylthiophthalimide (Phaltan); ethyl mercuric chloride mixtures (Ceresan); 3,5-dimethyl-2H-1,3,5-tetraydrothiadiazene-2-thione (Mylone); 1-naphthyl-N-methylcarbamate (Carbaryl); 1-dimethyl-carbamoyl-5-methyl-3-pyrazolyl dimethylcarbamate (Dimethilane); O,O-dimethyl S-(N-methylcarbamoyl methyl) phosphorodithioate (Dimethoate); 3-(3,4-dichlorophenyl)-1-methoxy-1-methylurea (Linutron); 2-chloro-4,6-bis(ethylamino)-S-triazine (Simazine); 1,1,1-trifluoro-2,6-dinitro-N, N-dipropyl-p-toluidine (Treflan or Trifluralin); 4-dimethylamino-3,5-xylyl N-methylcarbamate (Zectran); ferric dimethyl dithiocarbamate (Ferbam); N-1-naphthyl phthalamic acid (NPA); S-propyl-butylethyl thiocarbamate (PEBC); disodium methane arsenate (sodar); calcium acid methyl arsinate (calar); γ-benzenehydrochloride (Lindane); diethyl-S-diethylaminoethyl phosphorthiolate (Amiton or Amitrole); rotenone; pyrethrum; the acaricide of 2,4,5,4'-tetrachlorodiphenyl sulfone (Tedion); 1,1-dimethyl-piperidinium salts, e.g. Metiquat chloride and Terpal; the anionic salts of allyltrimethylammonium-, bromoethyltrimethylammonium-, isopropyltrimethylammonium, N-chloroethyl-N,N-dimethylhydrazonium-, N-bromoethyl-N,N-dimethylhydrazonium-, N-isopropyl-N,N-dimethyl-hydrazonium-, N-allyl-N,N-dimethylhydrazonium- and N,N-dimethylmorpholinium-cations and many more plant growth regulators and agricultural agents. Each of the above active adjuvants is individually effective at a range of rates, depending upon the particular substance, the particular use and the type of plant or soil and other growing conditions. Generally, these substances are employed individually at rates of between 0.001 and about 40 lbs. per acre. The same rate of application can be employed in the present invention when such chemically active additives are administered separately. When employed in admixture with the compounds of the present invention, or with either of separate solutions of the amide of the present complex or the haloalkylphosphonic acid solution, the known agent is preferably incorporated in an amount between about 0.01 weight percent and about 60 weight percent, based on the weight of the total composition. It is generally preferred that the known agricultural agent be used in an amount within its established rate range for individual use as sole agent, although because of the combined effect attributable to the present compounds, lesser amounts within the established rate range or amounts below the established rate range are appropriate. Thus, amounts below the median of the established rate range generally give good results in combination with the present complexes, particularly the chloroethylphosphonic acid/methylpyrrolidone complex.

The compounds and/or compositions of the present invention can be employed on many plants including gymnosperms and angiosperms, of monocotyledonous and dicotyledonous types. Species of these embrace vegetables, fruits, grasses, bushes, trees, ornamentals and the like. Examples of plant life which can be treated with the present compounds alone or in admixture include fruit trees such as apple, peach, apricot, tangerine, pear, cherry, grapefruit, orange, lemon, lime, plum, persimmon, banana, guava, nectarine, olive, papaya, date, fig, as well as fruits thereof and other trees such as oak, hazel, beach, pecan, almond, rubber, cork, pine, elm, spruce, fir, cedar, yew, eucalyptus, magnolia, dogwood, palm, walnut, willow, avacado, chestnut, hawthorn, maple, mango, and the like. Examples of vegetable plants suitably treated with the present compounds or their admixtures include asparagus, beans, brusselsprouts, carrots, cauliflower, celery, cucumber, squash, lentil, lettuce, onion, peas, peanut, peppers, potatoes, pumpkin, soybean, spinach, tomato, broccoli, kale, beets, and the like. Examples of grains and grasses which may be treated with the present compounds or their admixtures include barley, rye, oats, wheat, rice, corn, bluegrass, etc. Ornamentals suitably treated include rhododendron, roses, azelea, tulip, carnation, chrysanthemum, dahlia, hyacinth, geranium, impatien, iris, lily, poinsetta, snapdragon, fuchia, gladiola, etc. Other crops suitably treated with the present compounds or their admixtures include pineapple, melon, grapes, hops, berries, such as cranberries, strawberries, raspberries, blueberries, blackberries and currants, coffee plants, sugar cane, flax, cotton, tobacco plants and the like.

The compounds of the present invention induce the effects generally associated with ethylene activity, such as control of apical dominance and promotion of branching, bud initiation and enlargement, callus induction, increased resistance to cold, color and ripening promotion, breaking dormancy, inhibition of stem elongation; increased flowering and fruit set, advance or harvesting, resistance to lodging, disease resistance, loosening of fruit and nuts, dehiscence, promotion of rooting and rhizome development, seed development, increased yield in crops and other effects more fully discussed on pages 103 through 233 of Ethylene in Plant Biology by Frederick B. Abeles, published by the Academic Press, 1973.

By way of illustration, in the treatment of cotton plants to provide increased yield on single harvest and synchronization of boll opening and leaf drop, application of certain complexes, e.g. the acid/N-methyl pyrrolidone complexes (from about 1,000 ppm to about 15,000 ppm in a carrier) is preferably effected at least 30 days after square set; although it is to be understood that application can be made at any time after the square set up through initial boll break without any damage to the plant or plant fiber and still provide beneficial effect.

The present compound in the composition is applied to the crop at a temperature desirably within the range of from about 65° F. to about 95° F.; although application at higher or lower temperatures does not result in crop damage, but merely alters the period for plant response, which is extended at lower temperatures and shortened at higher temperatures. Normally, the results of the present application are evident within 5 to 14 days after treatment depending upon the concentration of the active ingredients and the temperature conditions extant. For example, with low level applications, results have been observed within 8 to 12 days; whereas at high level applications, results have been evident within 5 to 7 days. It has been found that field temperatures of about 95° F. and above generally do not require dosage levels above 3,000 ppm of the present compound, although higher dosage levels can be employed without damage to the plant or cotton fiber.

The advantages realized from the application of the above N-methyl pyrrolidone complexes for preharvest treatment of cotton are enumerated as follows:

1. Providing a multipurpose composition for effecting boll ripening, boll dehiscence and leaf defoliation so as to avoid the need for multiple chemical applications.
2. Increasing the rate of boll dehiscence so as to provide more uniformly opened bolls for first harvest collection and synchronizing defoliation so that it is effected after the bolls are fully developed and opening or opened.
3. Producing metabolic effects in increased dehiscence which exceeds the sum of the effects obtained with either the amide or the phosphonic acid from which the present complex compounds are formed.
4. Advancing early dehiscence of bolls containing mature fibers while having substantially no effect on the completely matured breaking bolls so as to increase the proportion of recoverable cotton in a single, first harvest and to minimize and/or obviate the necessity of a second harvest.
5. Providing cotton fiber of inherent high quality and, in certain cases, improving the quality of cotton fiber.
6. Reducing plant temperature sensitivity and resistance to low temperature dehiscence.
7. Permitting later planting of crop and/or earlier harvesting.
8. Providing economic and labor saving harvest of cotton crops.

A more detailed description of the treatment of cotton is set forth on pages 10 through 37 of applicant's copending application, Ser. No. 833,757 now abandoned which is based on actual experimentation and is incorporated herein by reference. The present compounds are stable, complexes, most of which are insoluble in diethyl ether and some are insoluble in water. All are ethylene releasing compounds and/or have profound ethylene stimulating capability when in contact with plant tissue.

The fact that the present compounds are distinct complexed compounds is shown by their infrared spectra, in which a shift of the amide carbonyl band from low to high wave length is indicative of complex formation, i.e. that there has been a change in the carbonyl structure. The infrared data for the complexes prepared in this study are given in Table I.

Further indication of the complex structure was provided by the base titration of the complexes in nonaqueous media. Table III reports the difference in $Ka_1$ and $Ka_2$ for the complexes versus ethephon. In Table II, a normal base titration gives the relative amount of ethephon in such complex on both a weight and molar basis. Further support for the complex structures was obtained from elemental analysis.

Another determination for the indicated structure of the complexes was made utilizing H1 and P31 nuclear magnetic resonance spectroscopy. Carbon 13 relaxation time (C-13, $T_1$) measurements indicated that the complex has a lifetime such that the present complex is characterized as a coordination or association complex as opposed to a collisional complex.

Finally, as a check on the character of the carbonyl group in the present complexes, carbon 13 analysis was made to provide a comparison between the carbonyls of the complexed and non-complexed compounds. These measurements indicated a downward shift for the complex which supports the structure as described herein.

Having thus generally described the invention, reference is now directed to the following examples which serve to illustrate preferred embodiments but which are not to be construed as limiting to the scope of the invention as set forth hereinabove and in the appended claims. In the examples all amounts and proportions are by weight unless otherwise indicated.

The preparation for each of the compounds shown below is reported in the Example designated by number. The same numbers are used throughout in analyses and testing to identify and illustrate utility of the indicated compound.

*Indicated Compound:

$$ClCH_2CH_2-\underset{\underset{H}{\overset{O}{|}}}{\overset{\overset{H}{\overset{|}{O}}\diagdown}{P}}\diagup\overset{\overset{R^1}{|}}{\underset{\underset{R^3}{}}{O-\overset{\pm}{N}-R^2}}$$

| Example No. | R¹ | R² | R³ |
|---|---|---|---|
| 2 | CH₃ | CH₃ | H |
| 4 | CH₃ | CH₃ | CH₃ |
| 5 | H | CH₃ | CH₃ |
| 6 | H | H | CH₃ |
| 9 | H | H | C₃H₅ |

*Indicated Compound:

$$ClCH_2CH_2-\underset{\underset{H-O}{|}}{\overset{\overset{H-O}{|}}{P}}\diagup\overset{\overset{R^1}{|}}{\underset{\underset{}{}}{O-\overset{+}{N}}}\diagdown\overset{R^5}{\underset{\underset{}{}}{C}}$$

| Example No. | R¹ | R⁵ |
|---|---|---|
| 1 | CH₃ | (CH₂)₃ |
| 3 | H | (CH₂)₃ |
| 7 | CH₃ | —CH=CH—CH=CH— |
| 8 | CH₃ | (CH₂)₄ |
| 10 | ⟨phenyl⟩-CH₃ | (CH₂)₄ |
| 11 | HOCH₂CH₂— | (CH₂)₃ |
| 12 | (CH₃)₂CH— | (CH₂)₃ |
| 13 | C₆H₁₁— | (CH₂)₃ |
| 14 | (CH₃)₃C— | (CH₂)₃ |
| 15 | CH₃(CH₂)₁₁— | (CH₂)₃ |
| 16 | Polyvinylpyrrolidone (K30) Complex | (CH₂)₃ |

*In the above, the "indicated compound" is that which is indicated by analysis and is therefore assumed; however, it is to be understood that the following Examples and Tables are not limited to this assumed structure but are directed to the complex compound of whatever structure results from the reaction between 2-chloroethylphosphonic acid, or indicated homolog, and the amide having the R¹, R² and R³ groups shown above.

EXAMPLE 1

A solution containing 2.97 grams (0.03 mole) of N-methyl-2-pyrrolidone in 7.13 grams (10 ml) diethyl ether was added, with stirring, to a solution containing 4.32 grams (0.03 mole) of 2-chloroethylphosphonic acid in 7.13 grams (10 ml) diethyl ether in a 250 ml glass Erlenmeyer flask equipped with a drying tube to maintain anhydrous conditions and a magnetic stirring bar to maintain gentle agitation. The reaction was effected at ambient temperature and atmospheric pressure. Within 10 minutes 6.48 grams of the zwitter ionic complex purported to have the structure shown above separated as a yellowish oil (88.7% yield).

The oil was recovered and dried in a rotary evaporator for 0.5 hours at 50° C. at 2 mm. The complex was subjected without further purification, to combustion analysis.

Calculated: C,34.53; H,6.16; N,5.75. Found: C,33.98; H,6.45; N,5.74.

The balance of the product in the ether phase could be isolated and recovered by evaporation of the diethyl ether solvent.

EXAMPLE 2

A solution containing 3.65 grams (0.05 mole) of N,N-dimethyl formamide in 7.13 grams (10 ml) diethyl ether was added, with stirring, to a solution containing 7.23 grams (0.05 mole) of 2-chloroethylphosphonic acid in 7.13 grams (10 ml) diethyl ether in a 250 ml glass Erlenmeyer flask equipped with a drying tube to maintain anhydrous conditions and a magnetic stirring bar to maintain gentle agitation. The reaction was effected at ambient temperature and atmospheric pressure. Within 10 minutes 9.2 grams of the zwitter ionic complex purported to have the structure shown above separated as a yellowish oil (84.6% yield). The oil was recovered and dried in a rotary evaporator for 0.5 hours at 50° C. at 20 mm. The complex was subjected, without further purification, to combustion analysis.

Calculated: C,27.59; H,5.98; N,6.44. Found: C,24.05; H,5.36; N,5.19.

The balance of the product in the ether phase could be isolated and recovered by evaporation of the diethyl ether solvent.

EXAMPLE 3

A solution containing 4.25 grams (0.05 mole) of 2-pyrrolidone in 7.13 gram (10 ml) diethyl ether was added, with stirring, to a solution containing 7.23 grams (0.05 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 10.0 grams the zwitter ionic complex purported to have the structure shown above separated as a yellowish oil (87.2% yield). The oil was recovered and dried in a rotary evaporator for 0.5 hours at 50° C. at 20 mm. The complex was subjected, without further purification, to combustion analysis:

Calculated: C,31.27; H,5.66; N,6.10. Found: C,30.53; H,5.74; N,5.79.

The balance of the product in the ether phase could be isolated and recoved by evaporation of the diethyl ether solvent.

EXAMPLE 4

A solution containing 4.35 grams (0.05 mole) of N,N-dimethyl acetamide in 7.13 grams (10 ml) diethyl ether was added, with stirring, to a solution containing 7.23 grams (0.05 mole) of 2-chloroethyphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 10.4 grams of a zwitter ionic complex purported to have the structure shown above separated as a yellowish oil (89.8% yield). The oil was recovered and dried in a rotary evaporator for 0.5 hours at 50° C. at 20 mm. The complex was subjected, without further purification, to combustion analysis: Calculated: C,31.10; H,6.48; N,6.05. Found: C,28.27; H,6.19; N,5.18.

The balance of the product in the ether phase could be isolated and recovered by evaporation of the diethyl ether solvent.

EXAMPLE 5

A solution containing 3.65 grams (0.05 mole) of N-methyl acetamide in 7.13 grams (10 ml) diethyl ether was added, with stirring, to a solution containing 7.23 grams (0.05 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 10.4 grams of the zwitter ionic complex separated as a yellowish oil (95.6% yield). The oil was recovered and dried in a rotary evaporator for 0.5 hours at 50° C. at 20 mm. The complex was subjected, without further purification, to combustion analysis:

Calculated: C,27.59; H,5.98; N,6.44. Found: C,26.87; H,6.02; N,5.95.

The balance of the product in the ether phase could be isolated and recovered by evaporation of the diethyl ether solvent.

EXAMPLE 6

A solution containing 2.95 grams (0.05 mole) of acetamide in 7.13 grams (10 ml) diethyl ether was added, with stirring, to a solution containing 7.23 grams (0.05 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 10.0 grams of the zwitter ionic complex purported to have the structure shown above separated as a yellowish oil (98.2% yield). The oil was recovered and dried in a rotary evaporator for 0.5 hours at 50° C. at 20 mm. The complex was subjected, without further purification, to combustion analysis:

Calculated: C,23.59; H,5.40: N,6.88. Found: C,23.22; H,5.59; N,6.74. The balance of the product in the ether phase could be isolated and recovered by evaporation of the diethyl ether solvent.

EXAMPLE 7

A solution containing 3.09 grams (0.028 mole) of N-methyl-2-pyridone in 7.13 grams (10 ml) diethyl ether was added, with stirring, to a solution containing 4.32 grams (0.03 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 6.30 grams of the zwitter ionic complex purported to have the structure shown above separated as a yellowish oil (87.6% yield). The oil was recovered and dried in a rotary evaporator for 0.5 hours at 50° C. at 20 mm. The complex was subjected, without further purification, to combustion analysis:

Calculated: C,36.44; H,5.23; N,5.19. Found: C,37.87; H,5.13; N,5.52.

The balance of the product in the ether phase could be isolated and recovered by evaporation of the diethyl ether solvent.

EXAMPLE 8

A solution containing 3.39 grams (0.03 mole) of N-methyl-2-piperidone in 7.13 grams (10 ml) diethyl ether was added, with stirring, to a solution containing 4.32 gram (0.03 mole) of 2-chloroethylphosphonic acid in 7.13 gram (10 ml) diethyl ether in a 250 ml glass Erlenmeyer flask equipped with a drying tube and a magnetic stirring bar. The reaction was effected at ambient temperature and atmospheric pressure. After a few minutes 5.7 grams of the zwitter ionic complex purported to have the structure shown above separated as a yellowish oil (73.7% yield). The oil was recovered and dried in a rotary evaporator for 0.5 hours at 50° C. at 20 mm. The complex was subjected, without further purification, to combustion analysis:

Calculated: C,34.63; H,6.64; N,4.80. Found: C,37.28; H,6.60; N,5.44.

The balance of the product in the ether phase could be isolated and recovered by evaporation of the diethyl ether solvent.

EXAMPLE 9

A solution containing 4.35 grams (0.05 mole) of N-propyl-formamide in 7.13 grams (10 ml) diethyl ether is added, with stirring, to a solution containing 7.23 grams (0.05 mole) of 2-chloroethylphosphonic acid in 7.13 grams (10 ml) diethyl ether in a 250 ml glass Erlenmeyer flask equipped with a drying tube and a magnetic stirring bar. The reaction is effected at ambient temperature and atmospheric pressure. After a few minutes 10.0 grams of the zwitter ionic complex purported to have the structure shown above separates as a yellowish oil (88.0% yield). The oil was recovered and dried in a rotary evaporator for 0.5 hours at 50° C. at 20 mm. The balance of the product in the ether phase could be isolated and recovered by evaporation of the diethyl ether solvent.

EXAMPLE 10

A solution containing 3.50 grams (0.02 mole) of N-(o-tolyl)-2-pyrrolidone in 7.13 grams (10 ml) diethyl ether was added, with stirring, to a solution containing 2.88 grams (0.02 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After a few minutes 5.30 grams of the zwitter ionic complex purported to have the structure shown above separated as a yellowish oil (81.4% yield). The oil was recovered and dried in a rotary evaporator for 0.5 hours at 50° C. at 20 mm. The balance of the product in the ether phase could be isolated and recovered by evaporation of the diethyl ether solvent.

EXAMPLE 11

A slurry of 3.87 grams (0.03 mole) of N-(2-hydroxyethyl)-2-pyrrolidone was added, with stirring, to 4.32 grams (0.03 mole) of 2-chloroethylphosphonic acid in a 250 ml glass Erlenmeyer flask. The reaction was effected at ambient temperature and atmospheric pressure. After 30 minutes 8.19 grams of the zwitter ionic complex indicated to have the structure shown above formed as a homogeneous yellowish oil (100% recovery).

EXAMPLE 12

A solution containing 2.54 grams (0.02 mole) of N-(isopropyl)-2-pyrrolidone in 7.13 grams (10 ml) diethyl ether was added, with stirring, to a solution containing 2.88 grams (0.02 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After 20 minutes the ether solvent was removed by evaporation and 5.40 grams of the zwitter ionic complex purported to have the structure shown above was recovered as a yellow oil and the oil dried in a rotary evaporator for 0.5 hours at 50° C. at 20 mm (100% recovery).

EXAMPLE 13

A solution containing 5.01 grams (0.03 mole) of N-cyclohexyl-2-pyrrolidone in 7.13 grams (10 ml) diethyl ether was added, with stirring, to a solution containing 4.32 grams (0.03 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After 30 minutes the ether solvent was removed by evaporation at reduced pressure and 9.30 grams of the zwitter ionic complex purported to have the structure shown above was recovered as a water insoluble, yellowish oil. The oil was recovered and dried in a rotary evaporator for 0.5 hours at 50° C. at 20 mm (100% recovery).

EXAMPLE 14

A solution containing 2.82 grams (0.02 mole) of N-(tert-butyl)-2-pyrrolidone in 7.13 grams (10 ml) diethyl ether was added, with stirring, to a solution containing 2.88 grams (0.02 mole) of 2-chloroethylphosphonic acid in 7.13 grams (10 ml) diethyl ether in a 250 ml glass Erlenmeyer flask equipped with a drying tube and a magnetic stirring bar. The reaction was effected at ambient temperature and atmospheric pressure. After 20 minutes the ether solvent was evaporated at reduced pressure, and 5.40 grams of the zwitter ionic complex purported to have the structure shown above was recovered as a water insoluble yellowish oil. The oil was recovered and dried in a rotary evaporator for 0.5 hours at 50° C. at 20 mm. (100% recovery).

EXAMPLE 15

A solution containing 2.54 grams (0.01 mole) of N-dodecyl-2-pyrrolidone in 3.57 grams (5 ml) diethyl ether was added, with stirring, to a solution containing 1.44 grams (0.01 mole) of 2-chloroethylphosphonic acid in 3.57 grams (5 ml) diethyl ether in a 250 ml glass Erlenmeyer flask equipped with a drying tube and a magnetic stirring bar. The reaction was effected at ambient temperature and atmospheric pressure. After 20 minutes the ether solvent was evaporated at reduced pressure and 3.40 grams of the zwitter ionic complex purported to have the structure shown above recovered as a water insoluble, yellowish oil. The oil was recovered and dried in a rotary evaporator for 0.5 hours at 50° C. at 20 mm. (100% recovery).

EXAMPLE 16

A solution containing 16.5 grams (0.15 mole) of polyvinylpyrrolidone (K30) in 54.6 grams of water was added, with stirring, to 28.9 grams of GAF technical grade 2-chloroethylphosphonic acid, containing 21.65 grams (0.15 mole) of 2-chloroethyl phosphonic acid, in a 250 ml glass Erlenmeyer flask. The reaction was effected with stirring at ambient temperature and atmospheric pressure. After a few minutes, the resulting aqueous solution contained 36.0% by weight of the zwitter ionic polymer purported to have the structure shown on the following page, was recovered and dried.

The polymeric product is believed to be primarily comprised of the monomer units:

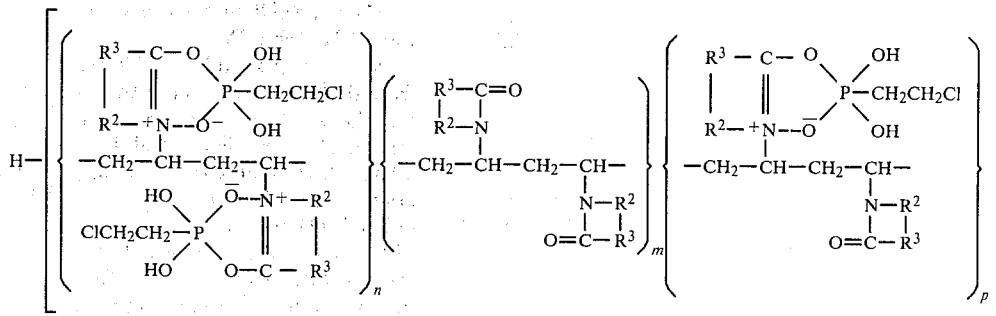

wherein each of n, m and p has a value of 0-500 and where at least one of subscripts n and p has a positive value, n being at least 1 when p is 0 and p being at least 2 when n is 0; which monomer units may occur in block or in random distribution in the polymer.

ANALYSIS

The above products were subjected to infrared analysis and the results reported in following Table I. The shift of the carbonyl amide indicates that the present compounds are complexes.

TABLE I

| Product of Example | Infrared Carbonyl Wave Length | | |
|---|---|---|---|
| | Complex Amide C = O ($\mu$) | Noncomplexed Amide C = O ($\mu$) | Difference ($\mu$) |
| 1 | 6.15 | 5.95 | 0.20 |
| 2 | 6.12 | 6.01 | 0.11 |
| 3 | 6.21 | 5.95 | 0.26 |
| 4 | 6.35 | 6.09 | 0.26 |
| 5 | 6.30 | 6.03 | 0.27 |
| 6 | 6.07 | 6.03 | 0.04 |
| 7 | 6.10 | 6.03 | 0.07 |
| 8 | 6.33 | 6.12 | 0.21 |
| 10 | 6.06 | 5.89 | 0.17 |
| 11 | 6.06 | 6.02 | 0.04 |
| 12 | 6.25 | 5.95 | 0.30 |
| 13 | 6.27 | 5.97 | 0.30 |
| 14 | 6.30 | 5.93 | 0.37 |
| 15 | 6.18 | 5.93 | 0.25 |

The complex structure of the present compounds was also determined by the CEPA* concentration in the product by titration in water with NaOH. The CEPA content and amide content is reported in following Table II.

*2-chloroethylphosphonic acid

TABLE II

CEPA CONTENT OF PRODUCTS AS DETERMINED BY TITRATION IN WATER

| Product of Example | Weight % CEPA | | Mole % CEPA | |
|---|---|---|---|---|
| | Found | Theory | Found | Theory |
| 1 | 60.74 | 59.34 | 51.46 | 50.00 |
| 2 | 66.66 | 66.44 | 50.25 | 50.00 |
| 3 | 64.53 | 62.96 | 51.69 | 50.00 |
| 4 | 62.04 | 62.42 | 49.60 | 50.00 |
| 5 | 65.35 | 66.44 | 48.79 | 50.00 |
| 6 | 64.67 | 71.01 | 42.83 | 50.00 |
| 7 | 57.30 | 56.56 | 50.53 | 50.00 |
| 8 | 54.07 | 56.12 | 47.93 | 50.00 |
| 10 | 48.22 | 45.40 | 52.25 | 50.00 |

TABLE II-continued
CEPA CONTENT OF PRODUCTS AS DETERMINED BY TITRATION IN WATER

| Product of Example | Weight % CEPA Found | Weight % CEPA Theory | Mole % CEPA Found | Mole % CEPA Theory |
|---|---|---|---|---|
| 11 | 52.99 | 52.83 | 50.16 | 50.00 |
| 12 | 53.77 | 53.39 | 50.38 | 50.00 |
| 13 | 46.98 | 46.39 | 50.59 | 50.00 |
| 14 | 50.85 | 50.44 | 50.06 | 50.00 |
| 15 | 36.30 | 36.51 | 49.77 | 50.00 |

Alcoholic solutions (methanol) of the complexed products are also titrated with a standard alcoholic (isopropanol) KOH solution and compared with similarly concentrated methanol solutions of CEPA titrated with the same standard KOH isopropanol solution. The titration results, reported in following Table III, show that there is substantially no difference between CEPA and the complex in the dissociation of the first P-OH bond ($Ka_1$), but that a significant difference between CEPA and the complex exists in the dissociation of the remaining P-OH ($Ka_2$). This difference also substantiates the formation of the present complexes, although the lack of difference in $Ka_2$ value does not indicate the absence of complex formation.

TABLE III
COMPARISON OF CEPA AND COMPLEX TITRATION WITH KOH IN ISOPROPANOL

| Product of Example | $Ka_1$ ($\pm 0.1 \times 10^{-4}$) | $Ka_2$ ($\pm 0.07 \times 10^{-10}$) |
|---|---|---|
| 1 | $1.26 \times 10^{-4}$ | $1.38 \times 10^{-10}$ |
| 2 | $1.41 \times 10^{-4}$ | $1.32 \times 10^{-10}$ |
| 3 | $1.07 \times 10^{-4}$ | $2.95 \times 10^{-10}$ |
| 4 | $1.00 \times 10^{-4}$ | $0.813 \times 10^{-10}$ |
| 5 | $1.26 \times 10^{-4}$ | $1.05 \times 10^{-10}$ |
| 6 | $1.32 \times 10^{-4}$ | $1.51 \times 10^{-10}$ |
| 7 | $1.12 \times 10^{-4}$ | $2.95 \times 10^{-10}$ |
| 8 | $0.83 \times 10^{-4}$ | $2.45 \times 10^{-10}$ |
| 10 | $1.31 \times 10^{-4}$ | $2.82 \times 10^{-10}$ |
| 11 | $0.79 \times 10^{-4}$ | $1.90 \times 10^{-10}$ |
| 12 | $0.98 \times 10^{-4}$ | $3.16 \times 10^{-10}$ |
| 13 | $1.00 \times 10^{-4}$ | $3.16 \times 10^{-10}$ |
| 14 | $0.89 \times 10^{-4}$ | $2.24 \times 10^{-10}$ |
| 15 | $0.76 \times 10^{-4}$ | $1.86 \times 10^{-10}$ |
| CEPA | $1.20 \times 10^{-4}$ | $0.86 \times 10^{-10}$ |

BIOLOGICAL ACTIVITY

The compounds of this invention are potent ethylene release agents and/or stimulate the in vivo production of ethylene by plants and plant tissue. Accordingly, these compounds exhibit standard physiological effects characteristic of ethylene. Examples of these effects are well known and include ripening; stunting; loss of apical dominance; germination; promotion, inhibition and sex reversal of flowers; leaf senescence, abscission, floral induction; etc., such as those effects indicated in Ethylene in Plant Biology by F. B. Abeles.

In both laboratory and field tests, the present compounds have shown that they strongly stimulate the in vivo production of ethylene as well as promote the effect of ethylene in field application. Some of the present compounds are more effective stimulators, on a per mole basis, than 2-chloroethylphosphonic acid.

EXAMPLES 17-29

The ability of the present products to stimulate ethylene generation was determined by the following procedures:

In a growth chamber maintained at 30° C. and 2,000 to 3,000 foot candle light, soybean plants from the same seed source were grown to the unifoliate state of development. Each of the following experiments were carried out in quadruplicate, and the results (found to be highly reproducible) were averaged and reported in following Table IV.

In each of Examples 17-29, sixteen leaf disc samples from the unifoliate plant sources were removed by cutting the leaf with a circular cork borer of 1.78 cm diameter. Each of the sixteen leaf discs were then floated for 30 minutes in a closed Petri dish on 25 ml of water as a control or with 25 ml of aqueous solutions containing either 1,000 ppm (Low Rate) or 3,000 ppm (High Rate) of the compound to be tested. At the end of 30 minutes, the leaf discs were removed from the solution, patted dry, and four each were reinserted in 4 10 ml vials fitted with a septum through which a syringe could be inserted for extracting a sample of the supernatant atmosphere. Four replicate gas samples for each compound were taken after the samples were allowed to stand in the light for one hour. The samples were analyzed for ethylene content by gas liquid phase chromatography. The vials were then placed in the dark for fifteen hours after which the gas above the leaf discs was resampled and analyzed in the manner similar to that described. The results, based on a comparison with the control, are reported in Table IV in nanoliters of ethylene per liter of atmosphere per $cm^2$ of leaf surface per mmole of test compound and are based on the average of four replicate samples.

TABLE IV

| Example | Compound of Example | Rate | nl Ethylene/liter/$cm^2$/mmole 1 hr (a) | nl Ethylene/liter/$cm^2$/mmole 15 hr (b) |
|---|---|---|---|---|
| 17 | 1 | Low | 6,720 | 21,904 |
|  |  | High | 6,690 | 17,496 |
| 18 | 2 | Low | 2,923 | 11,824 |
|  |  | High | 2,842 | 12,300 |
| 19 | 3 | Low | 4,202 | 16,919 |
|  |  | High | 2,859 | 13,863 |
| 20 | 4 | Low | 2,800 | 13,273 |
|  |  | High | 3,701 | 14,923 |
| 21 | 5 | Low | 2,195 | 14,586 |
|  |  | High | 3,631 | 16,078 |
| 22 | 6 | Low | 913 | 8,365 |
|  |  | High | 2,542 | 11,520 |
| 23 | 7 | Low | 4,368 | 15,647 |
|  |  | High | 4,991 | 14,681 |
| 24 | 8 | Low | 4,282 | 11,850 |
|  |  | High | 4,603 | 18,988 |
| 25 | 10 | Low | 3,379 | 15,311 |
|  |  | High | 6,912 | 15,268 |
| 26 | 11 | Low | 3,563 | 16,654 |
|  |  | High | 4,412 | 15,295 |
| 27 | 12 | Low | 3,743 | 15,090 |
|  |  | High | 4,805 | 14,264 |
| 28 | 16 | Low | 4,679 | 18,726 |
|  |  | High | 5,223 | 16,689 |
| 29 | 2-Chloroethylphosphonic Acid | Low | 4,912 | 15,944 |
|  |  | High | 4,876 | 14,035 |

Unifoliate Plants
(a) in light
(b) in dark
(c) untreated tissue (control) gave 125 nl ethylene/liter/$cm^2$ after 1 hour and 180 nl ethylene/liter/$cm^2$ after 16 hours.
Low = 1,000 ppm
High = 3,000 ppm

EXAMPLES 29-32

A field test was made as a comparison between Compound 1 and 2-chloroethylphosphonic acid (CEPA) in their relative ability to cause mature, green, flue-cured tobacco leaves to turn yellow and ripen. The results of this study are given in the following Table V.

In the field, 7 separate plots averaging 50 tobacco plants each, growing under the same conditions, were reserved for testing. The first two plots were sprayed with an aqueous solution of CEPA at a rate of 0.00687 lb. mole/acre and the results averaged and reported in Table V as Plot #1. Another two plots were sprayed with an aqueous solution of CEPA in the same concentration at a rate of 0.01374 lb. mole per acre (i.e. the standard commercial rate employed for CEPA) and the results averaged and reported in table V as Plot #2. Another two plots were sprayed with an aqueous solution of the complex product of Example I in the same concentration as those above at a rate of 0.00746 lb. mole/acre and the results averaged and reported in Table V as Plot #3. The final plot was left untreated as the control.

TABLE V

| Example Number | Plot Number | CEPA 1 lb. mole/acre | Compound of Example 1 lb. mole/acre | Days after treatment to produce a harvestable crop | Yield of Cured Tobacco lb./acre |
|---|---|---|---|---|---|
| 29 | 1 | 0.00687 | 0 | 15 | 2611 |
| 30 | 2 | 0.01374 | 0 | 4 | 2103 |
| 31 | 3 | 0 | 0.00746 | 4 | 2248 |
| 32 | Control | 0 | 0 | 21 | 2650 |

It is highly significant that the treatment with the compound of example 1 gave a 7% increase in yield over 2-chloroethyl phosphonic acid, (plot #2), which is the standard commercial rate for 2-chloroethyl phosphonic acid, and also provided a ripened harvestable crop within a quarter of the time required for CEPA, when CEPA and the compound of Example 1 are applied at substantially the same rate.

When the present compounds, for example the compounds of Examples 1 and 8, in a concentration of about 3,000 ppm in aqueous solution are sprayed to run off on rangy plants during their growing stage (e.g. an ornamental such as chrysanthenums or a member of the grass family such as corn), noticeable stunting (10-25%) of the mature plant results. The compounds of this invention possess many of the other plant growth regulating effects which are known and are attributed to ethylene. These effects are realized by the ethylene generating properties of the present compounds.

EXAMPLE 33

Apple Reddening

Four replicate groups of Cornell McIntosh fruit bearing apple trees were sprayed to run-off with the aqueous solutions noted in Table VI below. Another replicate group of trees was left untreated as a control. After one week, the apples were harvested and physical measurements taken. The replicate results were averaged and reported as follows:

TABLE VI

| Treatment | Rate mmoles/l | % Red Color |
|---|---|---|
| None | — | 36 |
| Ethephon | 0.248 | 63 |
| Ethephon | 0.497 | 67 |
| NMP/CEPA Complex | 0.270 | 69 |

TABLE VI-continued

| Treatment | Rate mmoles/l | % Red Color |
|---|---|---|
| NMP/CEPA Complex | 0.540 | 74 |

NMP is N-methyl-2-pyrrolidone and CEPA is 2-chloroethyl-phosphonic acid.

It has been found that 1.03 mmoles/liter of Ethephon is required to produce 72% reddening of Cornell McIntosh apples in a similar treatment (see Table II of the paper published in The Journal of American Society for Horticultural Science, Volume 99, #3, Page 239, May 1974).

EXAMPLE 34

Apple Reddening

Three groups of 4 year old Millersturdeespur apple trees (5 in each group) were sprayed to run-off with the aqueous solutions noted in Table VII below. Another group of 5 four year old trees was left untreated as a control. After two weeks, the apples were harvested and physical measurements taken. The replicate results were averaged and reported as follows:

TABLE VII

| Treatment | Rate mmoles/l | % Red Color |
|---|---|---|
| None | — | 33.3 |
| Ethephon | 0.248 | 38.1 |
| Ethephon | 0.497 | 58.4 |
| NMP/CEPA Complex | 0.270 | 64.2 |

NMP and CEPA are as defined above.

EXAMPLE 35

Walnut Loosening

Two groups of Ashley nut bearing walnut trees (5 trees in each group) were sprayed to run-off with the aqueous solutions noted in Table VIII. Another group of 5 trees was left untreated as a control. After 10 days, the replicate results were averaged and reported as follows:

TABLE VIII

| Treatment | Rate mmoles/Gal. | Leaf Fall | Harvestability % Removable |
|---|---|---|---|
| None | — | 0.0 | 50.0 |
| Ethephon | 0.0145 | 3.0 | 99.5 |
| NMP/CEPA Complex | 0.0078 | 1.2 | 86.0 |

NMP and CEPA are as defined above.

Of the Abscission ratings, 3 is considered excessive, 1 is considered slight and not harmful to the tree. The harvestability data in the above table was taken during normal harvest.

EXAMPLE 36

Sour Cherry Loosening

Two groups of Montmorency fruit bearing sour cherry trees (3 trees in each group) had their branches sprayed to run-off with the aqueous solutions noted in Table IX. Another group of 3 trees was left untreated as a control. After one week, replicate results were averaged and reported as follows. The fruit removal force measurements were made after seven days on a 100 fruit sample per replicate.

TABLE IX

| Treatment | Rate mmoles/1 | Fruit Removal Force, Grams |
|---|---|---|
| None | — | 445 |
| Ethephon | 1.375 | 281 |
| NMP/CEPA Complex | 0.716 | 278 |

NMP and CEPA are as defined above.

The above field test establishes that it requires about twice as much Ethephon to obtain a result approaching the present complex.

EXAMPLE 37

Filbert Loosening

Four groups of Barcellona nut bearing hazel trees (5 trees in each group) had their branches sprayed to run-off with the aqueous solutions noted in Table X. Another group of 5 trees was left untreated as a control. After two weeks, the replicate results were averaged and reported as follows:

TABLE X

| Treatment | Rate Moles/100 Gal. | % Drop |
|---|---|---|
| None | — | 13.8 |
| Ethephone | 1.31 | 30.7 |
| Ethephon | 2.61 | 42.9 |
| NMP/CEPA Complex | 1.87 | 50.8 |
| NMP/CEPA Complex | 2.82 | 55.0 |

NMP and CEPA are as defined above.

EXAMPLE 38

Grape Color Enhancement

Four groups of Zinfandel fruit bearing grape vines (5 vines in each group) were sprayed to run-off with the aqueous solutions noted in Table XI. Another group of 5 vines was left untreated as a control. The grapes were harvested when the control brix was 22% after which the grapes were juiced to give solutions from which optical density measurements could be made. The replicate results were averaged and reported as follows:

TABLE XI

| Treatment | Rate mmoles/1 | % Color |
|---|---|---|
| None | — | 50 |
| Ethephon | 3.93 | 91 |
| NMP/CEPA Complex | 2.45 | 100 |
| NMP/CEPA Complex | 0.67 | 71 |
| NMP/CEPA Complex | 0.09 | 39 |

NMP and CEPA are as defined above.

EXAMPLE 39

Sex Expression of Cucumbers

Two groups of Galaxy cucumbers (2 plants in each group) were sprayed to run-off after the first true leaf stage with the aqueous solutions noted in Table XII. Another group of 2 plants was left untreated as a control. The replicate results were averaged and reported as follows:

TABLE XII

| Treatment | Rate mmoles/1 | Male/Female Flower Ratio | Internode Distance*, Centimeters |
|---|---|---|---|
| None | — | 38.6 | 144 |
| Ethephon | 0.0412 | 8.8 | 131 |
| Ethephon | 0.1237 | 4.1 | 123 |
| NMP/CEPA Complex | 0.0445 | 3.4 | 117 |
| NMP/CEPA Complex | 0.1336 | 1.3 | 105 |

NMP and CEPA are as defined above.
*Total distance of 1-15 internodes.

In the above examples, it is to be understood that any of the other haloalkyl phosphonic acids included within the scope of Formula IV, such as for example the fluorinated, chlorinated, brominated or iodinated methyl, ethyl, propyl or butyl phosphonic acids, can be substituted in Examples 1 through 16 above to produce the corresponding complex product and that the product thus obtained can be substituted in any of the foregoing examples showing biological effects to provide compounds having similar utility. Moreover, any of the monoamides or polymers thereof included within the scope of those in Formula IV, such as N,N-diethyl butyramide, N-propyl butyramide, propamide, N-methyl propamide, N-methyl acetamide, N,N-dimethyl acetamide, acetamide, N,N-dimethyl formamide, N-ethyl acetamide, N-butyl acetamide, N-ethyl pyrrolidone, N-methyl-2-pyrrolidone, N-butyl-2-pyrrolidone, N-ethyl pyridone, N-methyl pyridone, N-propyl pyridone, 2-pyrrolone, N-methyl pyrrolone, N,N'-dimethylantipyrine, N-methyl piperidone, N-ethyl piperidone, N-naphthyl-2-piperidone, 2-piperidone, N-butyl piperidone, N-hydroxyethyl pyrrolidone, N-isooctyl pyrrolidone, N-isopropyl pyrrolidone, N-(o-tolyl) pyrrolidone, N-(2-trichloroethyl) pyrrolidone, polyvinyl pyrrolidone of between about 20,000 and about 550,000 number average molecular weight, vinyl-2-pyrrolidone dimer, trimer or tetramer, N-dodecyl pyrrolidone, N-cyclohexyl pyrrolidone, N-phenyl pyrrolidone, N-(2-chlorophenyl) pyrrolidone, N-naphthyl pyrrolidone, etc. can be substituted in Examples 1 through 16 above, which may also have substituted therein another haloalkyl phosphonic acid, to produce the corresponding compound, and the resulting product can be substituted in any of the foregoing examples showing biological effects to provide compounds having similar utility.

What we claim is:

1. The complex addition product of substantially equimolar amounts of 2-haloethylphosphonic acid and an amide selected from the group consisting of polyvinylpyrrolidone and amides of the formula:

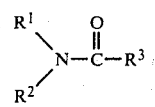

wherein $R^1$, $R^3$ and $R^2$ are independently selected from the group consisting of hydrogen, phenyl, napthyl, lower alkyl substituted phenyl, alkyl having from 1 to 24 carbon atoms, optionally substituted with hydroxy or halogen, and $R^1$ can be alkenyl having from 2 to 6 carbon atoms or wherein $R^2$ and $R^3$ taken together with the amido nitrogen can form a heterocyclic ring having from 3 to 5 carbon atoms.

2. The complex compound according to claim 1 wherein the amide reactant is a heterocyclic monoamide.

3. The complex according to claim 1 wherein the amide is polyvinylpyrrolidone having a number average molecular weight of between about 220 and about 550,000.

4. The complex according to claim 1 wherein the amide is N-methyl-2-pyrrolidone.

5. The complex according to claim 1 wherein the amide is N-methyl-2-pyridone.

6. The complex according to claim 1 wherein the amide is N-methyl-2-piperidone.

7. The process of contacting a plant or plant situs with a plant growth regulating amount of the complex product of claim 1.

8. A product of claim 1 wherein the complex is selected from the group consisting of a compound having the formula:

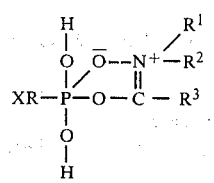

wherein R is lower alkyl; X is a halogen atom; $R^1$, $R^2$ and $R^3$ are each independently hydrogen, phenyl, napthyl, lower alkyl substituted phenyl, alkyl of from 1 to 24 carbon atoms, optionally substituted with hydroxy or halogen, and $R^1$ can also be alkenyl of from 2 to 6 carbon atoms, or wherein $R^2$ and $R^3$, together with N can form a N-heterocyclic ring having from 3 to 5 carbon atoms; and the polymer of the compound where $R^1$ is vinyl and $R^2$ and $R^3$, with N, form said heterocyclic ring; and the neutralized product of said compound.

9. The complex of claim 8 wherein R is ethyl, $R^1$ is hydrogen or methyl and $R^2$ and $R^3$, with nitrogen, form a heterocyclic ring having 4 to 5 carbon atoms.

10. The complex of claim 9 having the formula:

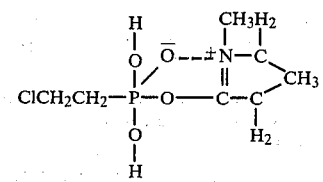

11. The complex of claim 9 having the formula:

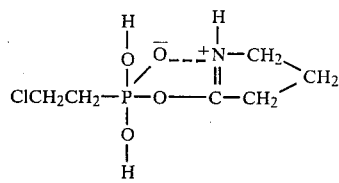

12. The complex of claim 9 having the formula:

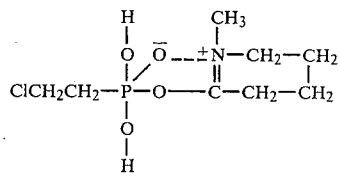

13. The complex of claim 9 having the formula:

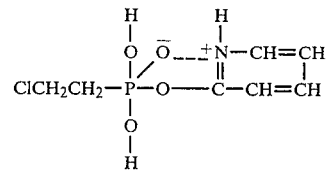

14. The complex of claim 8 having the formula:

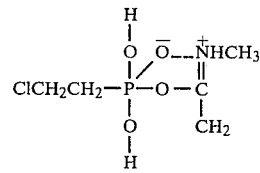

15. The complex of claim 8 having the formula:

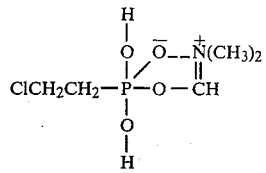

16. The complex of claim 8 wherein said amide is polyvinylpyrrolidone and said complex contains the monomeric units:

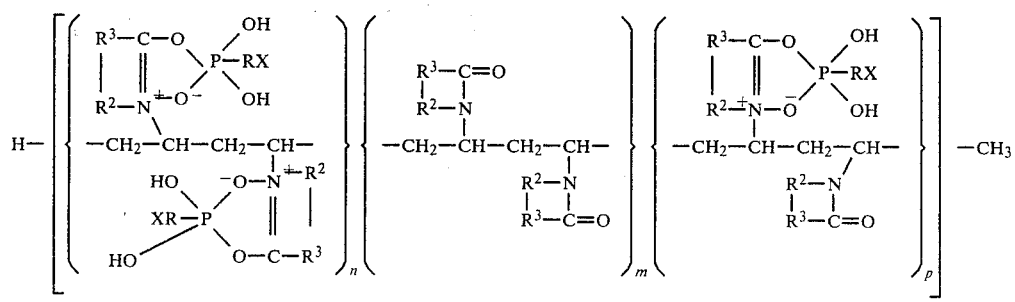

wherein each of n, m and p has a value of 0 to 5000 and where at least one of the subscripts n and p has a positive value, n being at least 1 when p is zero, and p being at least 2 when n is zero.

17. An ethylene generating agent represented by the complex compound of a 2-haloethylphosphonic acid and an amide selected from the group consisting of an amide having the formula:

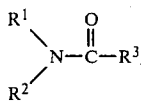

wherein $R^1$, $R^2$ and $R^3$ are as defined in claim 8 and the polymer of said amide where $R^1$ is vinyl and $R^2$ and $R^3$, with N, form said heterocyclic ring, having the formula:

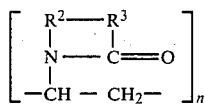

wherein n has a value of from 2 to 5000.

18. The complex of claim 1 wherein said haloethylphosphonic acid is 2-chloroethyl phosphonic acid and said amide is a cyclic mono-amide.

19. The 1:1 complex compound of 2-haloethyl phosphonic acid and N-methyl-2-pyrrolidone.

20. The process of contacting a plant or plant situs with a plant growth regulating amount of the complex of claim 8.

21. The process of contacting a plant or plant situs with a plant growth regulating amount of the complex of claim 19.

22. The process which comprises:
(a) contacting a haloalkyl phosphonic acid having the formula:

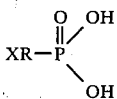

wherein X is a halogen atom and R is lower alkyl, and a compound selected from the group consisting of an amide having the formula:

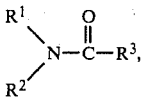

wherein $R^1$, $R^2$ and $R^3$ are as defined in claim 8 and the polymer of said amide where $R^1$ is vinyl and $R^2$ and $R^3$, with N, form said heterocyclic ring, having the formula:

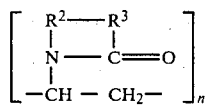

wherein n has a value of from 2 to 5000; and
(b) reacting said mixture at a temperature between about 0° C. and about 225° C. under from about 1 psig to about 150 psi to produce the complex of claim 1.

23. The process of claim 22 wherein said amide is a heterocyclic mono-amide.

24. The process of claim 22 wherein said amide is linear.

25. The process of claim 22 wherein said amide is polyvinylpyrrolidone.

26. The process of claim 22 wherein said amide is N-methyl-2-pyrrolidone.

27. The process of claim 22 wherein said amide is N-methyl-2-pyridone.

28. The process of claim 22 wherein said amide is N-methyl-2-piperidone.

29. The process of claim 22 wherein said amide is N,N-dimethyl formamide.

30. The process of claim 22 wherein said amide is acetamide.

31. The process of claim 23 wherein the amide has an unsaturated ring.

32. The process of claim 23 wherein the amide has a saturated ring.

33. The process of claim 22 wherein the reaction is carried out in the presence of an organic solvent and the reaction mixture forms a product layer, and a solvent layer when the reaction is completed and the product is recovered by phase separation.

34. The process of claim 22 wherein the reaction is carried out in the presence of water and the product is recovered by evaporation of water or by phase separation.

35. The process of claim 34 wherein the water is evaporated to provide a reaction product containing at least 2 moles of the complex to 3 moles of water.

36. The process of claim 34 wherein the water is removed to form a substantially anhydrous complex reaction product.

37. The process of claim 22 wherein the complex is under substantially anhydrous conditions.

38. The process of contacting a plant or plant situs with a plant growth regulating amount of the complex of claim 16.

* * * * *